(12) United States Patent
Dunn et al.

(10) Patent No.: US 8,690,927 B2
(45) Date of Patent: Apr. 8, 2014

(54) BONE FIXTURE ASSEMBLY

(75) Inventors: Raymond Dunn, Shrewsbury, MA (US);
Kristen Billiar, Worcester, MA (US);
Janice Lalikos, Worcester, MA (US);
Alexander Christakis, West Brookfield, MA (US); John Dieselman, Scituate, MA (US)

(73) Assignee: University of Massachusetts, Boston, MA (US)

( * ) Notice: Subject to any disclaimer, the term of this patent is extended or adjusted under 35 U.S.C. 154(b) by 307 days.

(21) Appl. No.: 13/071,155

(22) Filed: Mar. 24, 2011

(65) Prior Publication Data
US 2012/0253407 A1 Oct. 4, 2012

Related U.S. Application Data

(63) Continuation-in-part of application No. PCT/US2010/032269, filed on Apr. 23, 2010.

(60) Provisional application No. 61/172,060, filed on Apr. 23, 2009.

(51) Int. Cl.
*A61B 17/80* (2006.01)

(52) U.S. Cl.
USPC ........... 606/286; 606/289; 606/291; 606/292; 606/295; 606/296; 606/301; 606/305; 606/307

(58) Field of Classification Search
USPC ......... 606/280, 281, 286, 289, 291, 292, 295, 606/296
See application file for complete search history.

(56) References Cited

U.S. PATENT DOCUMENTS

| | | | |
|---|---|---|---|
| 4,484,570 A * | 11/1984 | Sutter et al. | ............ 606/282 |
| 4,854,311 A | 8/1989 | Steffee | |
| 5,536,127 A | 7/1996 | Pennig | |
| 6,319,254 B1 | 11/2001 | Giet et al. | |
| 2002/0016595 A1 | 2/2002 | Michelson | |
| 2002/0128654 A1* | 9/2002 | Steger et al. | ............ 606/69 |
| 2002/0156477 A1 | 10/2002 | Knopfle et al. | |
| 2004/0220569 A1 | 11/2004 | Wall et al. | |
| 2005/0065521 A1 | 3/2005 | Steger et al. | |
| 2005/0209599 A1 | 9/2005 | Brunsvold | |
| 2008/0140128 A1 | 6/2008 | Smisson et al. | |
| 2008/0161861 A1 | 7/2008 | Huebner | |
| 2010/0145388 A1 | 6/2010 | Winslow et al. | |
| 2010/0152856 A1 | 6/2010 | Overes et al. | |
| 2010/0174314 A1 | 7/2010 | Mirkovic et al. | |
| 2010/0174326 A1 | 7/2010 | Selover et al. | |
| 2010/0185247 A1 | 7/2010 | Richelsoph | |
| 2010/0191291 A1 | 7/2010 | Phan et al. | |
| 2010/0198268 A1 | 8/2010 | Zhang et al. | |
| 2010/0199483 A1 | 8/2010 | Justis et al. | |
| 2010/0204798 A1 | 8/2010 | Gerbec et al. | |
| 2010/0217328 A1 | 8/2010 | Terrill et al. | |
| 2010/0228301 A1 | 9/2010 | Greenhalgh et al. | |

* cited by examiner

*Primary Examiner* — Nicholas Woodall
(74) *Attorney, Agent, or Firm* — McCarter & English, LLP

(57) ABSTRACT

An assembly for rigid bone fixation includes a plate and a screw. The screw can be rotated freely within the plate in a non-locking configuration to secure the plate against the bone. A locking mechanism is engaged to prevent the screw from moving relative the plate. In one embodiment, the plate includes a threaded portion and a non-threaded portion. The screw head rotates within the non-threaded portion to tighten the screw and pull the plate against the bone. The locking mechanism can include a moveable nut that rotates within the threaded portion of the plate to lock the screw and plate in a locking mode. The locking mechanism can include a second screw to actuate and expansion portion of screw inserted into the bone. The assembly can be used for rigid fixation of bones that experience cyclic loads, such as the sternum and mandible. Methods of rigid bone fixation are also described.

14 Claims, 13 Drawing Sheets

BONE FIXTURE ASSEMBLY

CROSS-REFERENCE TO RELATED APPLICATION

This application is a continuation-in-part which claims the benefit of U.S. Provisional Application No. 61/172,060 filed on Apr. 23, 2009 and International Application No. PCT/US2010/032269 filed Apr. 23, 2010 the entire contents of the above applications being incorporated herein by reference.

BACKGROUND OF THE INVENTION

Nearly 700,000 open heart surgeries are performed annually in North America. During the surgery, the sternum is bisected to access the thoracic cavity, a procedure known as sternotomy. Following the primary operation, the sternum is closed, typically with wire sutures.

The sternal reapproximation procedure is generally successful. However, post operative complications occur in approximately 2% of procedures, generally in patients over the age of 65. High instances of osteoporosis that are common in this age group causes the sternum to wear away at fixation points, causing loosening within the system. When loosening occurs, other complications can arise, such as medianstinitis, or infection of the sternum, which has been shown to have a mortality rate as great as 15%.

Low cyclic forces generated by repetitive motion, such as breathing motion in the case of the sternum, can lead to unwanted loosening and even failure of the fixation system. This problem becomes even more acute in the case of osteoporotic or lower-density bones. Currently the most common practice of sternal fixation utilizes stainless steel surgical wires. However, for some patients, the low cyclic forces generated by breathing can cause the wires to cut into the patient resulting in losses of fixation and normal bone alignment. Rigid fixation techniques, such as with a plate and screw assembly, are known, but are not commonly used for sternum fixation. This is due to a variety of factors, including the length of time for the procedure and increased level of skill required by the surgeon, as well as the cost. In addition, existing plate and screw assemblies are not optimized for fixation of the sternum.

SUMMARY OF THE INVENTION

The present invention relates to a bone fixation device and more specifically to sternum fixation with a screw and plate assembly. The screws pull the plate to the bone and have a locking capability. No micro-movement issues occur as with an unlocked beveled screw where the angle of the screw can be off axis and generate movement of the bone relative to the plate.

A preferred embodiment enables higher torque which decreases loosening of the assembly over time. The screw/head interface minimizes wedge angle effect. A preferred embodiment uses a higher number of threads for improved purchase in cortical bone as well as increased depth of threads for improved purchase in cancellous bone. The locking mechanism inhibits sawing effect which can degrade the fixation given the repetitive loading experienced by many bone structures during healing.

In one embodiment, the outer diameter of the screw is generally equal to the plate hole inner diameter, which helps minimize initial loosening. A cap is used to secure the screw to the plate after the screws have secured the plate into position against the bone surface.

The preferred embodiment further includes a method of securing fractured bone elements together and/or repairing surgically separated bone elements in accordance with the devices and methods described herein.

A further preferred embodiment relates to a method of manufacturing a bone fixation device as set forth herein.

BRIEF DESCRIPTION OF THE DRAWINGS

Other features and advantages of the present invention will be apparent from the following detailed description of the invention, taken in conjunction with the accompanying drawings of which.

DETAILED DESCRIPTION OF THE INVENTION

Figure 1:
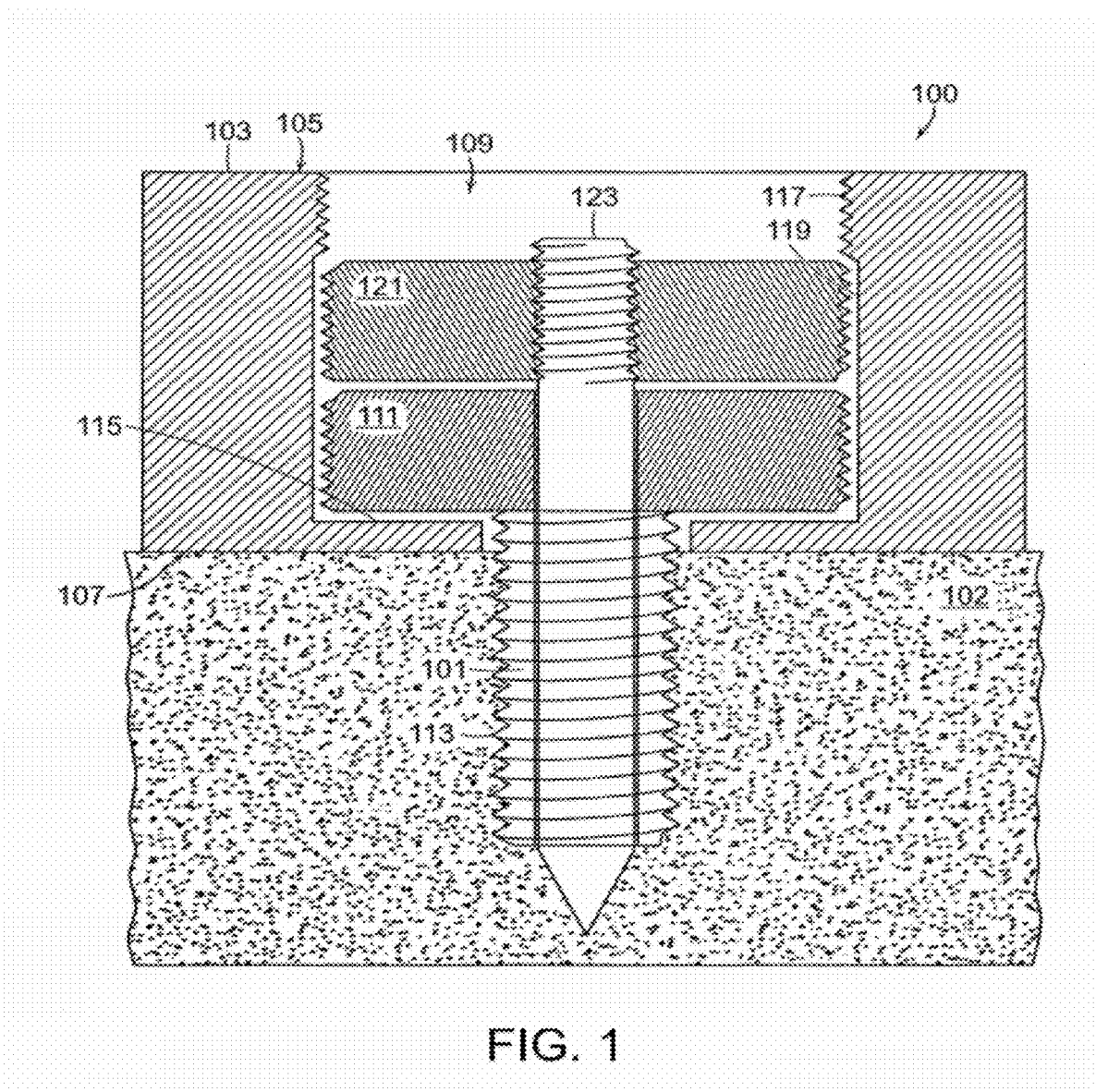
FIG. 1 is a side schematic illustration of a screw and plate assembly according to one embodiment of the invention.

This application claims the benefit of U.S. Provisional Application No. 61/172,060, filed on Apr. 23, 2009, and also of International Application No. PCT/US2010/032269 filed Apr. 23, 2010, the entire contents of the above application incorporated herein by reference.

Referring to FIGS. 1-5, an assembly 100 for rigid bone fixation, and in particular, fixation of a sternum, includes a screw 101 and a plate 103. The plate 103 has a first surface 105 and a second surface 107 and an opening 109 extending through the plate 103. The screw 101 is a bone screw having a head portion or flange 111 and a threaded portion 113. In a bone fixation procedure, the second surface 107 of the plate 103 is positioned adjacent to a bone portion 102. The threaded portion 113 of the screw 101 is inserted through the plate opening 109 and screwed into the bone 102 to anchor the plate 103 to the bone. The first threaded portion 113, or screw shaft, can have a length of between about 0.4-1.4 cm with an outer diameter of ~4 mm, an inner diameter of ~2 mm, and a preferred range of pitch of 1-1.25 mm. For other applications, such as mammalian leg bones, the mandible bone or other bone fixture applications, the pitch or distance between the threads (thread spacing) can be in a range of 0.8 mm to 1.6 mm. The depth of the threads can be in a range of 1.5 mm to 2.5 mm. In general, the plate 103 has a plurality of openings 109 (see, e.g., FIG. 8B), and a plurality of screws 101 are inserted through the openings 109 to anchor the plate 103 to respective bone portions 102 in order to physically hold the bone portions together, limiting their movement and facilitating bone healing. In one embodiment, the present plate and screw assembly 100 is used for rigid fixation of a human or animal sternum.

In one embodiment, shown in FIG. 1, the opening 109 in the plate 103 has a first, larger diameter proximate the first surface 105 and a second, smaller diameter proximate the second surface 107. The threaded portion 113 of the screw 101 extends through the smaller diameter portion of the opening 109 and into the bone portion 102. The head portion or flange 111 of the screw is received within the larger diameter portion of the opening 109, but is prevented from passing completely through the opening 109 by a shoulder portion or plate retainer 115. The retainer 115 has a planar surface that contacts a planar surface of the flange 111.

The plate opening 109 has a threaded portion 117 and an unthreaded portion 119. The threaded portion 117 (e.g., tapped M8×1.24, "I" drill, 0.272") extends partially along the opening in the axial direction, and is generally adjacent to the first surface 105 of the plate 103. The unthreaded portion 119 of the opening 109 extends between the threaded portion 117 and the shoulder 115.

Figure 2C:
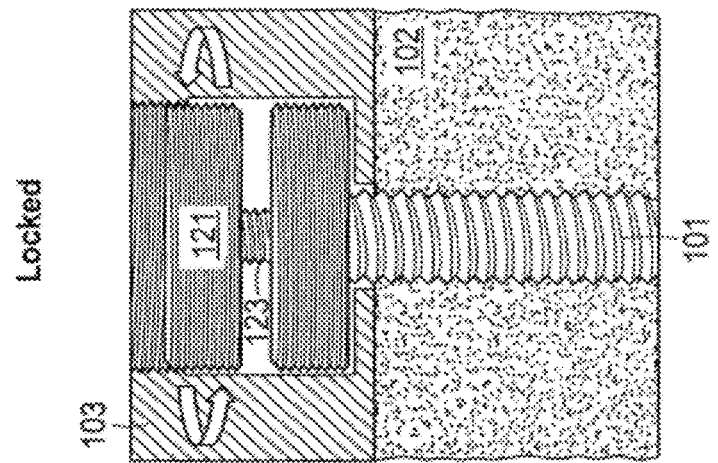
FIGS. 2A-2C schematically illustrate the locking of the screw to the plate.
Figure 2B:
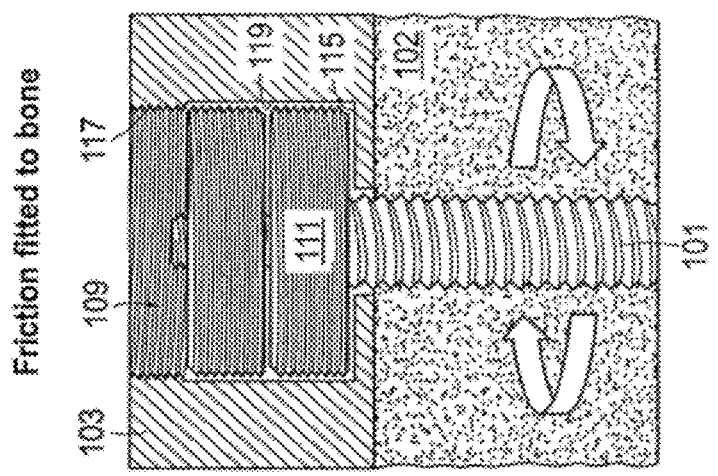
Figure 2A:
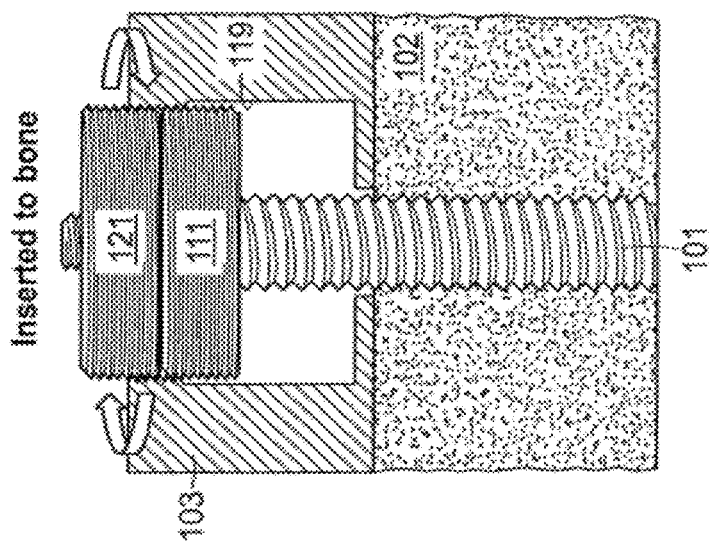

The head portion 111 of the screw 101 is threaded (e.g., M8×1.25 Die, 8 mm diameter), and threads into the threaded portion 117 of the plate opening 109. In operation, as shown in FIGS. 2A-2C, for example, the screw 101 is screwed into the plate 103 using the matching threaded portions of the screw head 111 and the threaded portion 117 of the plate 103 (FIG. 2A). The screw head 111 clears the threaded portion 117 of the plate opening 109 and enters into the unthreaded portion 119 of the opening 109 which provides a non-limiting free space (FIG. 2B). With no thread interactions between the screw 101 and plate 103, the screw 101 can be fastened without plate restriction to increase the pressure of the plate 103 to the bone portion 102 (e.g., sternum). Here, the screw 101 can be rotated as much as desired, and a friction fit can be achieved. At this point, the assembly 100 is non-locking.

Figure 3A:
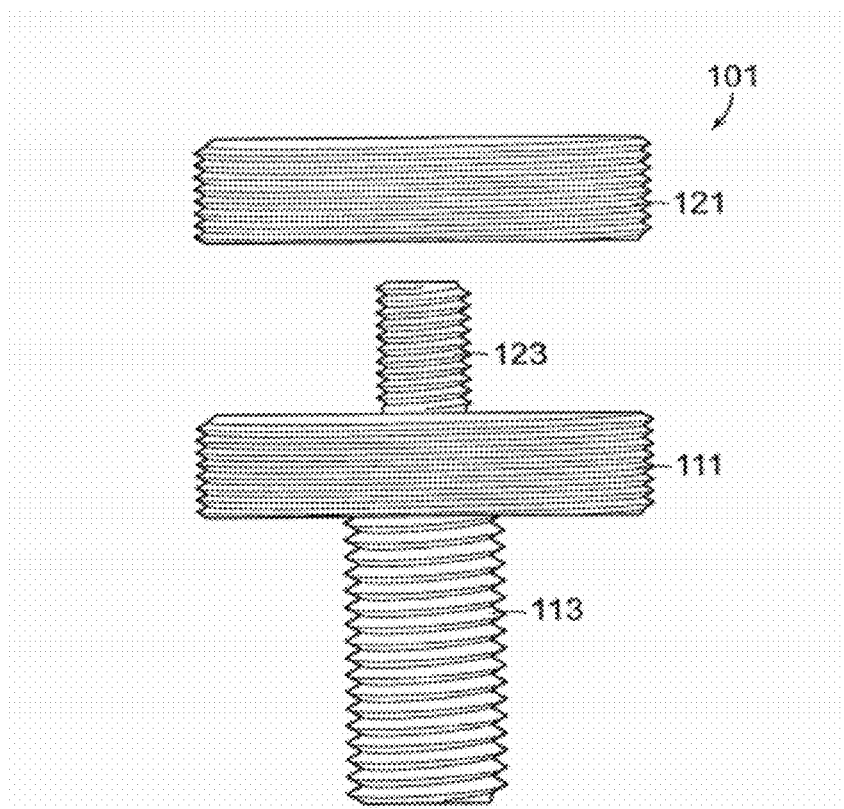
FIGS. 3A and 3B are profile views of the bone fixation screw according to one embodiment.
Figure 3B:
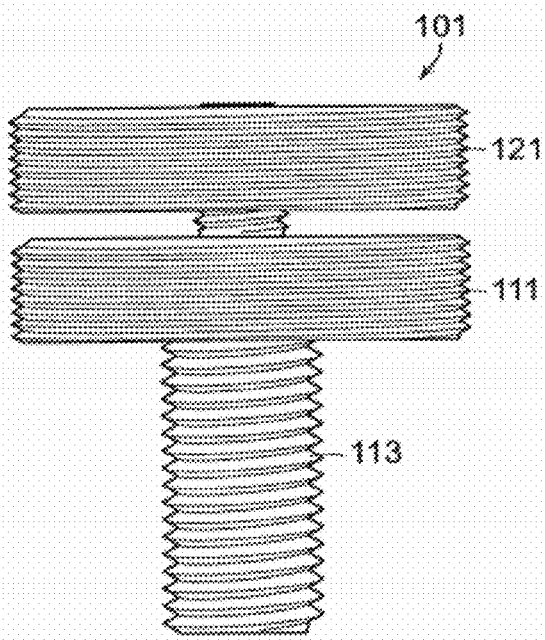

The screw 101 can further include a locking mechanism. In the embodiment of FIGS. 1-5, for example, the screw 101 includes a moveable nut 121 on the head portion 111. The nut 121 has the same outer diameter (e.g., 8 mm) and external threading (e.g., M8×1.25 die) as the head portion 111. The nut 121 also includes internal threads (e.g., M3×0.5 tap, #39 tap drill, 0.0995"), and is threaded to a threaded projection 123 (e.g., M3×0.5 die, 3 mm diameter) that extends from the top of the screw 101, as shown in FIGS. 3A and 3B.

As shown in FIGS. 2A and 2B, the nut 121 is adjacent to and generally flush with the threaded portion of the head 111 while both components pass through the initial threaded portion 117 of the plate opening 109 and arrive in the unthreaded free-space portion 119 of the plate opening 109 as a single unit. The screw 101 can thus rotate limitlessly in free-space so long as the nut 121 and head 111 remain in this single-unit configuration. The torque feedback of the screw 101 is only from the bone 102 and is not influenced by the plate threads. The screw head 111 engages the plate 103 at the shoulder 115 and the rotation of the screw 101 pulls the plate 103 into intimate contact with the bone 102.

Once the screw 101 has reached the target torque and is ready to lock to the plate 103, the nut 121 is deployed by rotating it relative to the threaded projection 123 on the top of the screw 101. This rotation is in the opposite direction from the direction of rotation during insertion of the screw into the plate. This rotation causes the nut 121 to "back up" (i.e., move up on the threaded projection 123) and re-engage with the threaded portion 117 of the plate opening 109. This is illustrated in FIG. 2C.

In one embodiment, the exterior threads of the nut 121, which engage with the plate threads, are different from the interior threads that engage the nut with the projection 123 on the screw 101. The threads can have slightly different pitch, for example, so that during the backing up of the nut 121, the difference in threads causes the nut to bind or lock up and provide backpressure to the screw. The assembly 100 is then locked. The locking can be accomplished within a half to a full turn of the nut 121.

The screw/plate assembly 100 allows a full friction fit in addition to restricting screw loosening in the plate.

To remove the screw 101, the nut 121 is rotated back down the threaded projection 123 and onto the top of the head portion 111. This unlocks the screw 101 from the plate 103. The entire screw 101 can then be rotated in the reverse direction of FIG. 2A to remove the screw from the bone and plate.

Figure 4A:
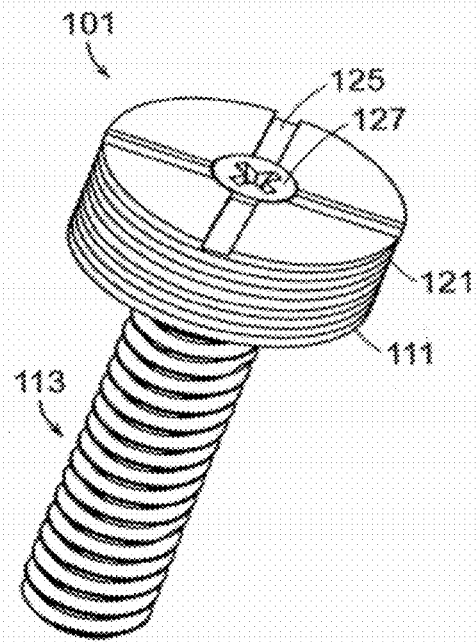
FIGS. 4A and 4B are perspective views of the bone fixation screw.
Figure 4B:
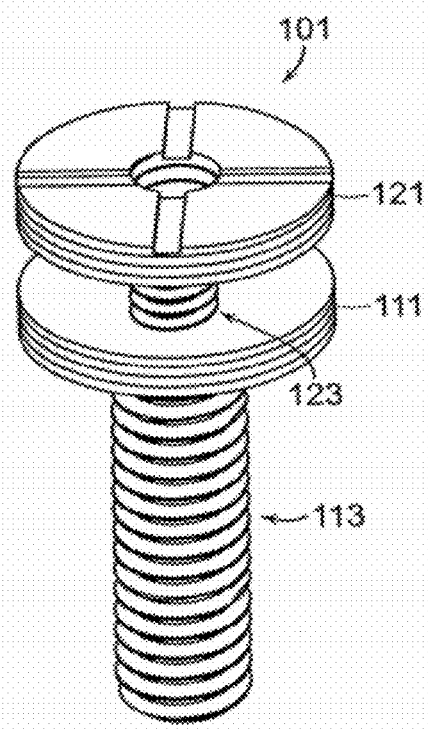
Figure 5:
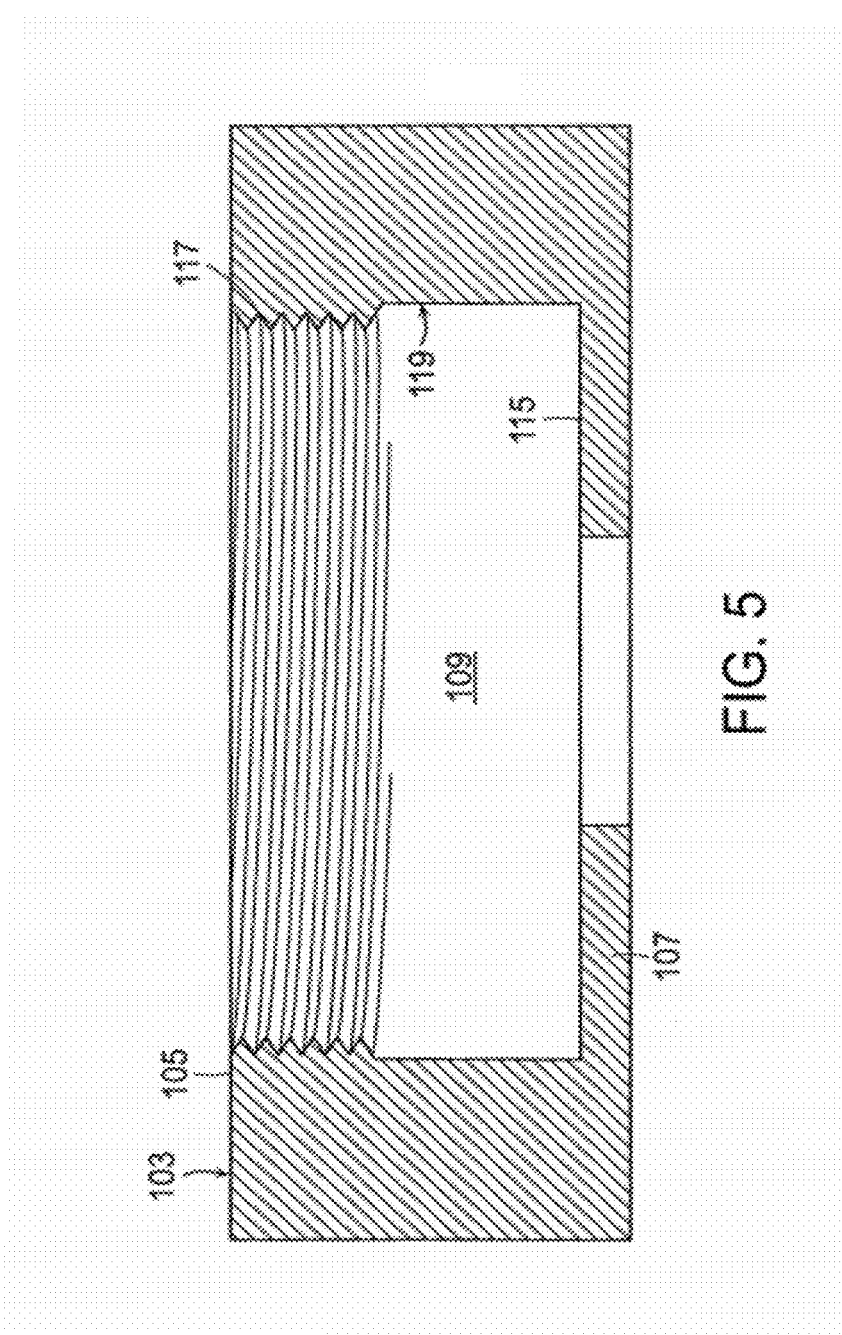
FIG. 5 is a cross-sectional view of the plate.

As shown in FIGS. 4A and 4B, the nut 121 and threaded projection 123 can include respective grooves 125, 127 or other features to enable the screw 101 and nut 121 to be rotated together during insertion and removal of the screw 101, as well as for the nut 121 to be rotated separately for locking and unlocking of the screw to the plate.

In the embodiment of FIGS. 1-5, the interface between the screw 101 and plate 103 is substantially planar, though it will be understood that alternative configurations, such as a beveled or rounded interface can be employed. An advantage of certain embodiments is that the locking mechanism restricts relative motion between the screw 101 and the plate 103 in the axial direction, which prevents undesirable rotation or "wobbling" of the screw relative to the plate and minimizes or eliminates micro-motion issues.

In another embodiment, only the nut 121 includes external threads that mate with the threaded portion 117 of the plate opening 109, and the head portion 111 of the screw 101 is unthreaded. This embodiment operates substantially as described above in connection with FIGS. 1-5.

Figure 6:
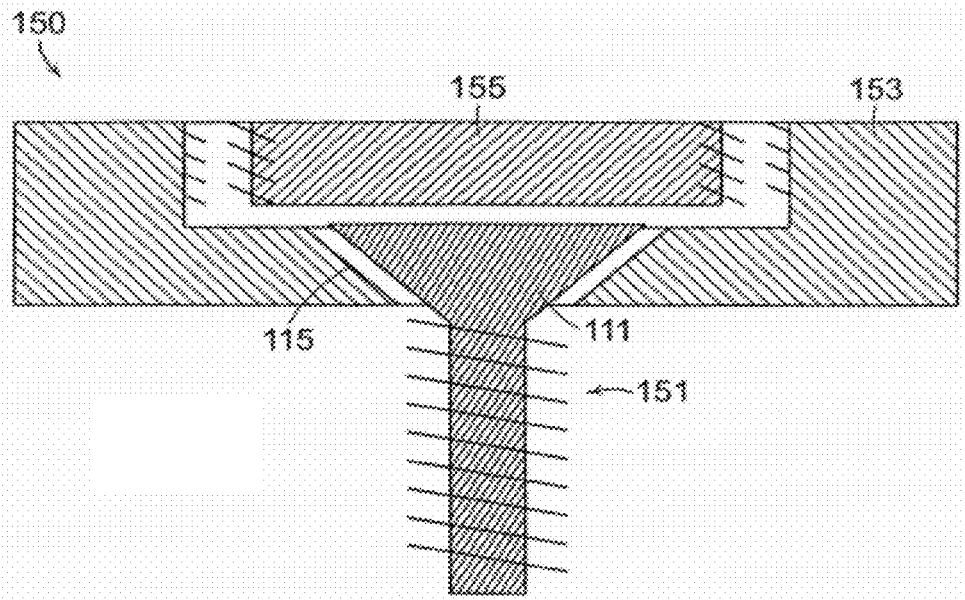
FIG. 6 illustrates yet another embodiment of a screw and plate assembly having a threaded plate and locking cap.

FIG. 6 illustrates yet another embodiment of a screw and plate assembly 150 having a threaded plate 153 and locking cap 155. In this embodiment, the screw 151 is not threaded on the head portion of the screw. The screw 151 is inserted through the plate hole and tightened, with the screw head being received by a beveled shoulder in the plate 153. Once the screw 151 is sufficiently tightened, a locking cap 155 having external threads is threaded onto the plate 153. The cap 155 prevents the screw 151 from rotating or wobbling relative to the plate 153.

The screw and plate can be made from any suitable biocompatible materials. In general, the materials have high-strength and are generally rigid, although some flexibility and compliance may be beneficial. Suitable materials include, for example, titanium and stainless steel.

Figure 7:
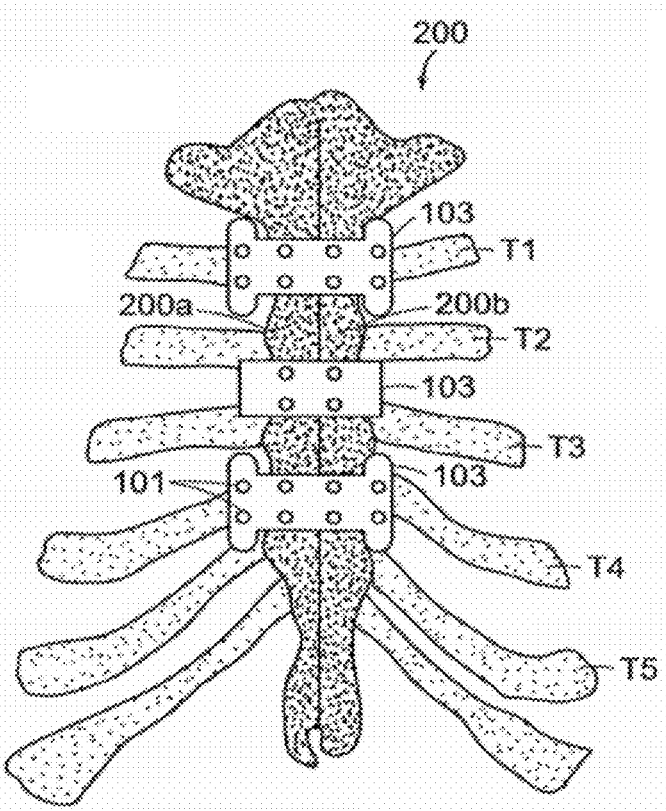
FIG. 7 illustrates a sternum closed by rigid plate fixation.

The present invention is directed to a method of rigid fixation of a sternum. The anatomy of an adult human sternum 200 is shown in FIG. 7. The sternum is also known as the breastbone and occupies the central anterior thorax. In conjunction with the first seven pairs of ribs, it encapsulates the heart and lungs. The average length of the sternum in adults is 17 cm. Because the sternum encloses the lungs, it must be capable of flexing during inhalation and expiration. Thus, the sternum contains a high percentage of spongy trabecular cancellous bone, with a thin cover shell of dense, compact cortical bone.

In a sternotomy procedure, the sternum is bisected longitudinally along its center and retracted to access the thoracic cavity. Once the primary operation is complete, the surgeon follows with sternal fixation, in which the halves of the sternum are fixed together so that the bone will heal properly. In one embodiment, a method of rigid sternum fixation uses a plate and screw assembly such as shown and described in connection with FIGS. 1-6. An example of a sternum 200 closed by rigid plate fixation is illustrated in FIG. 7. A plurality of plates 103 are affixed to the sternum 200 using screws 101 and hold the two halves 200a, 200b of the sternum in place while it heals. Each plate 103 is fixed to the bone using a plurality of screws 101 inserted through holes in the plate. Generally, at least three and preferably four or more screws, distributed on either side of the sternum bisection, are utilized to attach the plate. Rigid plate fixation offers advantages over other techniques, such as wire fixation, because it physically holds the bone portions together during the healing process, limiting their relative movement and not disrupting the blood supply in the region.

Figure 8A:
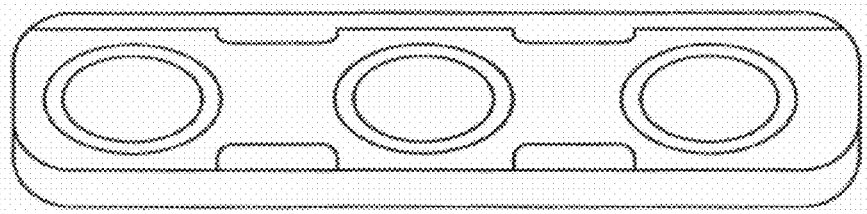
FIG. 8A illustrates a straight plate.
Figure 8B:
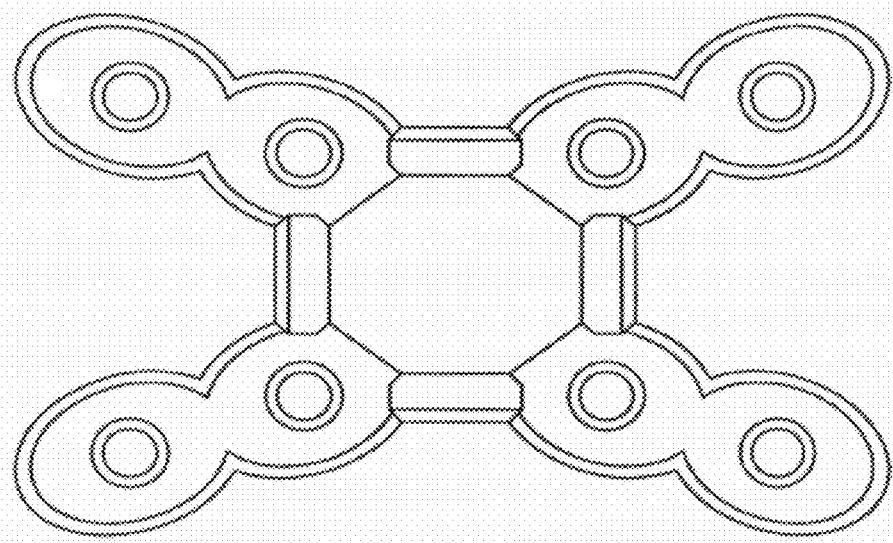
FIG. 8B illustrates an X-shaped plate.

Plates are usually designed and manufactured specifically for a clinical application. Due to the large variety of bone shapes and sizes within the body, there are several different types of rigid fixation plates that can be used. For example, there are straight plates, X-shaped plates, wave plates, and friction plates. FIGS. 8A and 8B illustrate exemplary embodiments of a straight (FIG. 8A) and an X-shaped (FIG. 8B) plate.

X-shaped plates may be an effective option for sternal fixation due to the fact that they enable multiple screws to pass through the center of the bone.

Wave plates are a variation of the straight fixation plate, and are widely used in long bone compression fixation. These plates are beneficial because they do not apply compressive forces directly to the fracture site. Applying extensive compressive forces to the wound site can increase vascular disruption to the wound site, limiting the blood supply to the wound site and increasing healing time. Although this design is usually applied to large cortical bones, it can be useful for decreasing the healing time of a very vascular bone such as the sternum.

The friction (or adhesive) plate system adds ridges to the undersurface of the plate, increasing the plate-bone contact area and effectively decreasing the stresses on the screws used in the system by as much as a third. These plates come in a variety of shapes and sizes, and can be added to almost any plate and screw system, creating a very versatile system. By minimizing the motion between the plate and the bone, stress protection in that region of bone can be greatly reduced. Although this system has not been widely accepted, it can be very advantageous for sternal fixation, since the screws that are used are much smaller and have much more cyclic loading than plate systems elsewhere in the body.

Figure 9:
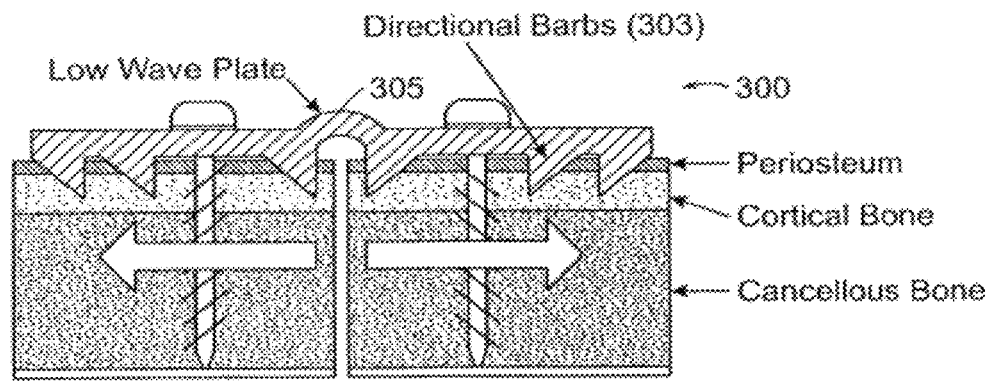
FIG. 9 illustrates a friction wave plate with directional barbs.

In one embodiment, a rigid fixation assembly includes a friction wave plate 300 as schematically illustrated in FIG. 9. The plate 300 has directional barbs 303 that distribute the lateral loads over the entirety of the plate to bone surface. By including these small anchors, the press fit may be slightly relaxed to improve bone vascularity. The concern of a locking system leveraging is reduced since the plate does not solely rely on one point of purchase, but on many distributed points. The center break where the sternum halves reunite include a slight wave 305 to guarantee no pressure is compromising the healing factors.

Rigid bone fixation is possible mainly due to a large variety of bone screws, and over the past 20-30 years the bone screw has become the most commonly used orthopedic implant device. Without these screws, many types of rigid fixation would be much less effective or even impossible. Each type of screw is uniquely designed for its specific clinical purpose. Several parameters are taken into consideration when choosing a screw, including the health of the bone at the wound site (osteoporotic or healthy), the location of the fracture (long bone, short bone, flat bone etc), the density of the bone (cortical or cancellous) and they type of fracture. A majority of orthopedic bone screws are categorized as cortical or cancellous, partially or fully threaded, solid or cannulated, self-tapping or non-self-tapping.

The cortical or cancellous properties of the screw are determined based on the density of the bone that the screw is being applied to. Cortical screws are very similar to metal screws found in a local hardware store—they have a very high thread count, with a very low thread depth and pitch. Because they are used in the hardest, highest density type of bone, thread penetration is not very important, but it is vital that the threads stay in constant contact with the bone surrounding it. Conversely cancellous screws are very similar to wood screws, boasting deeper thread penetration to maximize stabilization in the low density cancellous bone.

Stabilization of an implant or plate is greatly dependant on the bone-screw interface. The screws in a rigid fixation system function as stabilizers by exerting a compressive force on the plate and onto the bone. The screws also provide resistance to shear forces when the plate is loaded axially. The different parts of the screw (e.g., head, core and thread) serve to achieve the functions of providing compressive force and maintaining purchase in the bone material. The head of the screw functions to transmit the insertion torque to the core and threads and to provide a stop when the head contacts the bone surface. Once the screw head has contacted the bone, the torque exerted on the threads through the head generates a compressive force. In locking plate systems, the head is also threaded such that it locks into respective threads on the plate. This system limits the torque to which the screw can be tightened as well as prevents wobble of the screw.

The core is the screw shaft that the threads wrap around. A screw is defined by a major diameter that is measured from the outside of the threads on one side to the outside of the threads on the other as well as a minor diameter that defines the smallest diameter of the shaft at the base of the threads that represents the core. The length of the core is of particular interest in its application to the sternum. Screws can be categorized as unicortical or bicortical (in which the end of the screw is embedded into the innermost cortical layer). Bicortical insertion can provide greater stability with respect to both wobble and pullout, but can also cause damage to the bone and to tissue and/or organs beyond the bone.

The screw thread is defined by its depth (difference between the major and minor diameter) and its pitch. The thread depth is what responsible for thread purchase as it represents the area of the screw that is interacting with the bone. The thread is a helical ridge that is wrapped around the core. Its function is to convert rotation into translational movement. The cross section is a series of ramps. Together with the helical shape, when rotated the triangular cross section functions as an inclined plane that provides a mechanical advantage in moving through the bone and to maintain a compressive force. The thread pitch is defined as the distance between threads on the screw.

Figure 10:
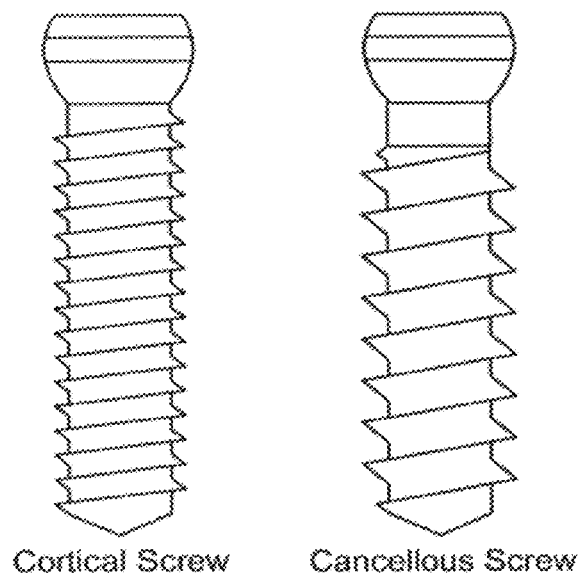
FIG. 10 illustrates cortical and cancellous screws.

Screw anatomy can be modified to work most effectively in different types of bone. The use of screws in bone fixation has directed screw design to either cortical or cancellous application. Cortical screws are designed for purchase in dense bone with shallow threads cut at about 60° and decreased pitch. Cancellous screws typically follow a wood screw's design that includes a tapered outside diameter for easier insertion and wider threads to increase purchase in less dense and compressive bone. Each of these screw types can be seen in FIG. 10.

When coupled with a plate, the screw design becomes more complicated. For internal fixation of fractures, the plate and screw system should hold any force that would normally be applied to the bone while maintaining its position. This loading can happen in two ways, either by the frictional contact between the plate and the bone or the interaction between the shaft of the screw and the bone. If the primary mechanism of loading relies on the screws, than the contact interface between the plate and the shaft of the screw may cause the screw to bend in cyclic loading. Screw bending will rapidly result in the early fatigue failure of the screw. Because of this, the preferred mechanism of loading is for the plate to be friction fit with the cortical bone.

Rigid fixation methods are used throughout the body, however as previously discussed, they are not commonly practiced on sternum. There are many screw plate systems each designed to accommodate a specific bone's aspect, such as pelvic plating systems, which allow screws to be installed at various angles to maximize rigidity. However, the sternum is different from other bones due to the continuous applied loads from breathing. Additionally, the sternum cannot be voluntarily immobilized during the recovery period. In order to identify the effective options for rigid sternal fixation, the mechanisms of loosening and failure due to lateral cyclic loads can be investigated.

Cyclic testing was performed to compare the performance of commercially available screw types for rigid sternum fixation. Testing was also performed using an embodiment of a present plate/screw assembly that allowed locking of the screw after a complete friction fit is achieved.

Four non-fixed human sternums with varying degrees of osteoporosis were bisected lengthwise and cut laterally into strips. Bone fixation plates were attached to the samples and cyclically loaded. Cyclic testing was performed using an Electroplus E-1000 uniaxial mechanical test device (Instron®). Testing consisted of cycling between 0 and 50 N at a rate of 2 Hz for 15,000 cycles. The bone pieces were potted in a PVC cap with epoxy. A custom grip was used to hold and vertically load the plate. Local distraction between the plate was measured using an extensometer.

Figure 11:
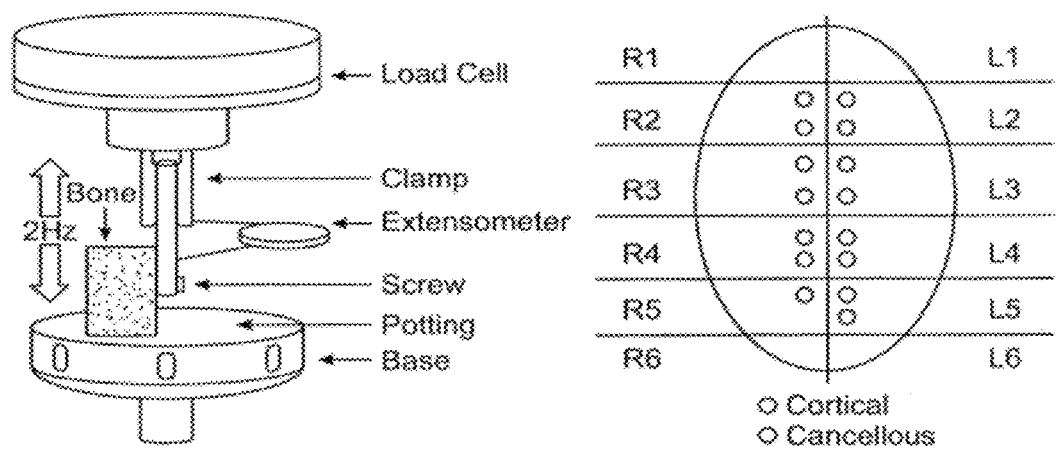
FIG. 11 illustrates the testing setup for cyclic load testing of sternum fixation devices.
Figure 12:
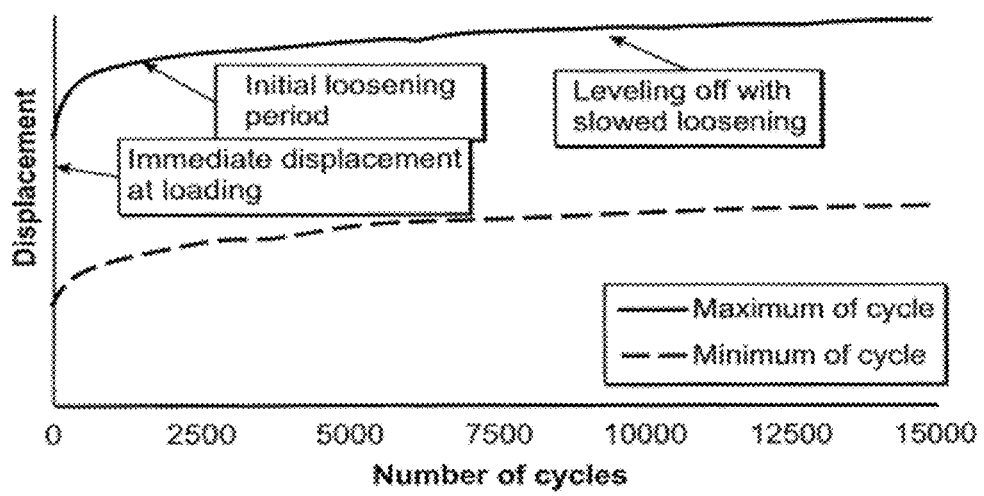
FIG. 12 is a displacement curve resulting from cyclic loading of a sternum fixation device.

Cancellous and cortical pelvic screws and pedicle screws with locking and non-locking heads provided by Stryker® were cyclically tested. An example of the present plate/screw assembly (Embodiment A) was also tested. The screws were paired and tested down the length of the sternum. FIG. 11 illustrates the testing setup.

MicroCT measurements with a resolution of 15 μm were made on each sample to determine the local bone density and to view the mechanism of loosening within the bone.

The initial (10 cycle) and final (15,000 cycle) displacement data were analyzed statistically using a two-way ANOVA with screw type and bircortal or unicortal purchase as the factors (p<0.05 considered significant).

Most of the loosening was observed in the first 10 cycles. After approximately 2000 cycles, where is a slow increase in displacement that continues for the next 13000 cycles. A typical displacement curve resulting from cyclic loading is shown in FIG. 11.

In the initial 10 cycles, the displacement of screw types were not significantly different. Though unicortical attachment had a significantly larger displacement compared to bicortical (1.05 mm vs. 0.36 mm, p=0.015). The screw type appears to affect the final displacement following the 15,000 cycles more so than the number of cortices anchored. The mean data of groups is expressed in Table 1.

TABLE 1

Summary of displacement data (mm, mean ± SD)

| | Unicortical Purchase | | | | |
|---|---|---|---|---|---|
| | Pelvic Cancellous | Pedicle Locking | Pedicle Cortical | Pelvic Cortical | Embodiment A |
| Initial | 1.43 ± 0.411 | 0.261 ± 0.022 | 0.534 ± 0.501 | 1.01 ± 0.555 | 0.183 ± 0.084 |
| Final | 2.69 ± 0.104 | 1.54 ± 0.69 | 1.57 ± 1.23 | 1.15 ± 0.721 | 0.458 ± 0.182 |

| | Bicortical Purchase | | |
|---|---|---|---|
| | Pelvic Cancellous | Pedicle Cortical | Pelvic Cordical |
| Initial | 0.421 ± 0.102 | 0.216 ± 0.129 | 0.256 ± 0.127 |
| Final | 3.31 ± 1.65 | 0.355 ± 0.313 | 0.625 ± 0.584 |

The final mean displacement of cancellous screws was significantly larger than cortical (2.60 mm vs. 1.17 mm, p=0.039). The Embodiment A screw outperformed the others, often with a lower final displacement (after 15,000 cycles) than the initial displacement of the other groups (at 10 cycles).

The findings indicate that both screw type and cortical purchases are important parameters for a screw-plate system for sternal closure in osteoporotic patients. Though the sternum is mostly cancellous bone, osteoporotic cancellous bone is generally too weak for adequate fixation. Pullout test within the cancellous region of the sternum quantified the low strength of this bone. Cortical screws demonstrate greater resistance to transverse loading due to additional thread purchase into the cortical layers.

Bicortical purchase minimized displacement during cyclic loading by two mechanisms. First, the screw is loaded against two relatively rigid structures changing the loading from a singe to double shear model, limiting screw wobbling and bone damage. Second, the total amount of thread purchase in cortical bone increases.

However, bicortial purchase may not be clinically recommended due to the risk of injuring the heart. Unicortical locking screws can be used to restrict screw wobbling, yet once secured to the plate it cannot be further tightened it cannot be further tightened to the bone thus limiting the friction fit. Unicortical non-locking screws provide a friction fit, but are susceptible to wobbling and early loosening.

The plate/screw assembly of one embodiment of the present invention advantageously utilizes a non-locking screw with a post-locking mechanism that changes between a non-locking and locking mode. As discussed above, the screw is fastened into a partially threaded plate past the threaded portion of the hole and into the threadless free space. At this time with no thread interactions, the system is non-locking and the screw may be fastened without restriction to achieve friction fit. When the screw is ready to be locked in the plate, a locking mechanism is engaged. This system satisfies the goal of allowing a full friction fit in addition to restricting screw loosening in the plate.

In one embodiment, the present screw includes a cortical pitch with increased thread depth. A screw design specifically for the sternum, which is composed of cancellous bone between two layers of cortical bone, includes screw parameters designed for both cortical and cancellous bone types. It is important in cancellous bone to have as much bone as possible captured between the screw threads for maximum purchase as larger volumes of bone surrounding the screw increases resistance to backout. Screw parameters such as thread depth, shape, and pitch can be designed for specific types of cancellous bone to optimize this volume.

Figure 13:
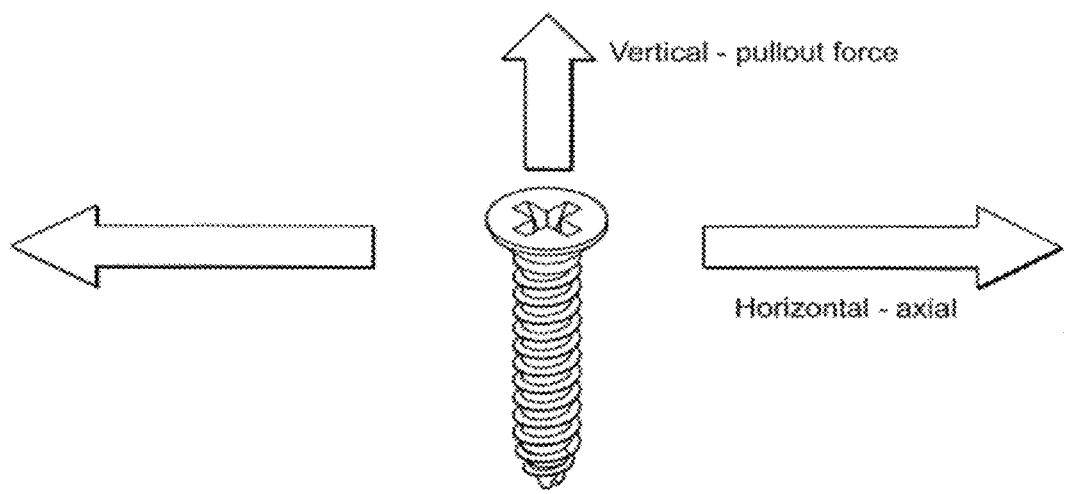
FIG. 13 schematically illustrates the loading forces on a screw.

The loosening of screws is due to two types of forces, as shown in FIG. 13. Vertical forces result in pullout of the screws while horizontal, or axial, loading forces, results in loosening through force passed through the plate, which places stress on the bone, cutting it over cyclic loading.

The rigid sternal fixation design is comprised of a plate and screw interface. Multiple screws anchor the rigid plate against the sternum halves. The design consists of three interfaces that influence mechanical loading: screw to plate, screw to bone, and plate to bone. The design alternatives are based off the design criteria and the mechanisms of loosening identified from the tests.

The screw to plate interface is concerned with the degree of freedom the screw is permitted after installation. A conventional locking screw and plate limits the pressure of the plate to the bone due to premature locking. If the plate is floating atop and not securely pressed against the bone, the cyclic forces apply additional leverage against the bone. By using a non-locking mechanism the plate can be pressed against the bone as much as the screw can be tightened. However a screw that locks into the plate remains rigid.

The Stryker pelvis plate systems, for example, were designed to allow the screw to freely pivot approximately 30° within the plate. Experimental results indicate this pivoting mechanism provides poor rigid fixation. The screw is designed to be loaded traverse, however if the screw is pivoted to a certain extent the screw is loaded similar to a pullout. As the screw pivots the softer cancellous bone becomes gouged and destroyed. Screws that maintain a permanent angle with the plate distribute the cyclic forces evenly throughout both the cortical and cancellous bone.

Accordingly, the screw to plate interface should keep the screw at a fixed angle in the plate. One option to achieve this is to use a thicker plate with a fitted shoulder directing the screw perpendicular to the plate. Another design incorporates an additional locking cap component. A non-locking screw is installed followed by a threaded cap that provides direct parallel pressure to the cap of the screw preventing any pivoting or motion once. A third design is similar to the second however rather than an additional screw on cap, a thin rigid bar is slid into place.

The results indicate cortical threads minimize displacement better than cancellous threads. Even though the sternum is composed more of cancellous than cortical bone, the cancellous region being osteoporotic does not exhibit significant structural integrity. The screw design is primarily focused on achieving the greatest fixation in the cortical bone layer. The cancellous screws had an insufficient number of threads in the cortical bone; a high thread density screw permits greater thread surface to cortical bone. The screw threads are the primary fixation source of the entire plate system and must securely bite into the cortical bone.

The thread design should maximize cortical surface contact, generally with only one cortex, and make do with the spongy cancellous region. One screw design uses a high thread density with a smaller outer diameter at the tip. The smaller diameter is intended to lightly anchor into the second cortical layer, while the remaining screw is wider and fixates to the remaining bone. Another design maintains a constant outer diameter size with a decreasing inner diameter, in which the screw core tapers in the distal direction of the screw cap. A third design has a lower thread density to offer enough distance for the threads to curve slightly backwards, acting as barbs clinching against the bone. Yet another design uses a corkscrew as a means of gripping into the bone as opposed to threads.

The interface between the plate and the bone consists of the surface area contact when the plate is compressed against the bone. In the effort to minimize local distraction between the bone halves a plate that resists shear loading against the bone is desirable. In certain embodiments, this can be achieved through use of a friction plate. In the specific case of a sternotomy, the periosteum covering the sternum is not usually removed, resulting in indirect contact of the plate and the bone. The plate to bone tightness generally depends on the fixation of the screw, however a higher friction coefficient reduces the plate sliding on the periosteum of the sternum option proposed having a plate with similar roughness to a filer.

Excessive pressure against the bone from another surface may increase a vascularity causing osteonecrosis. This interface has clashing constraints with the need for press-fit to prevent screw plate leveraging while simultaneously ensuring the bone properly heals.

Figure 14:
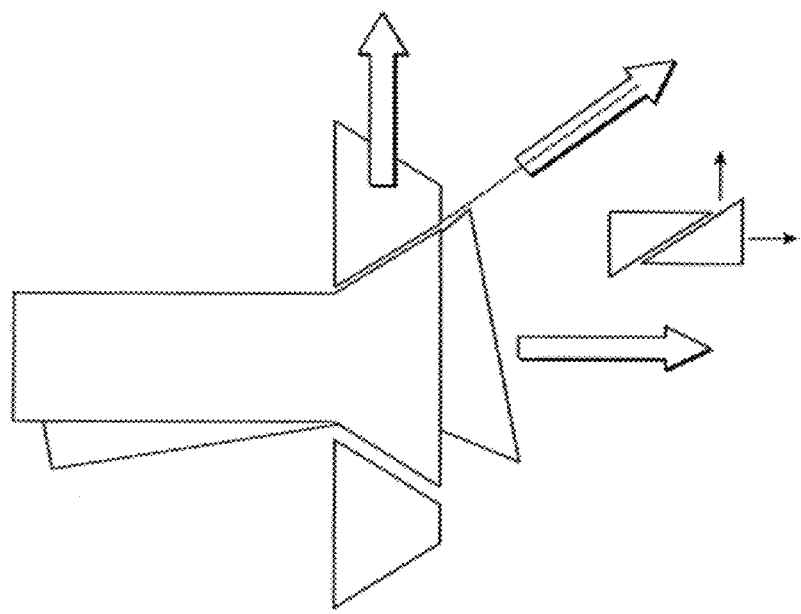
FIG. 14 illustrates the motion of a screw and plate having a wedge interface.
Figure 15:
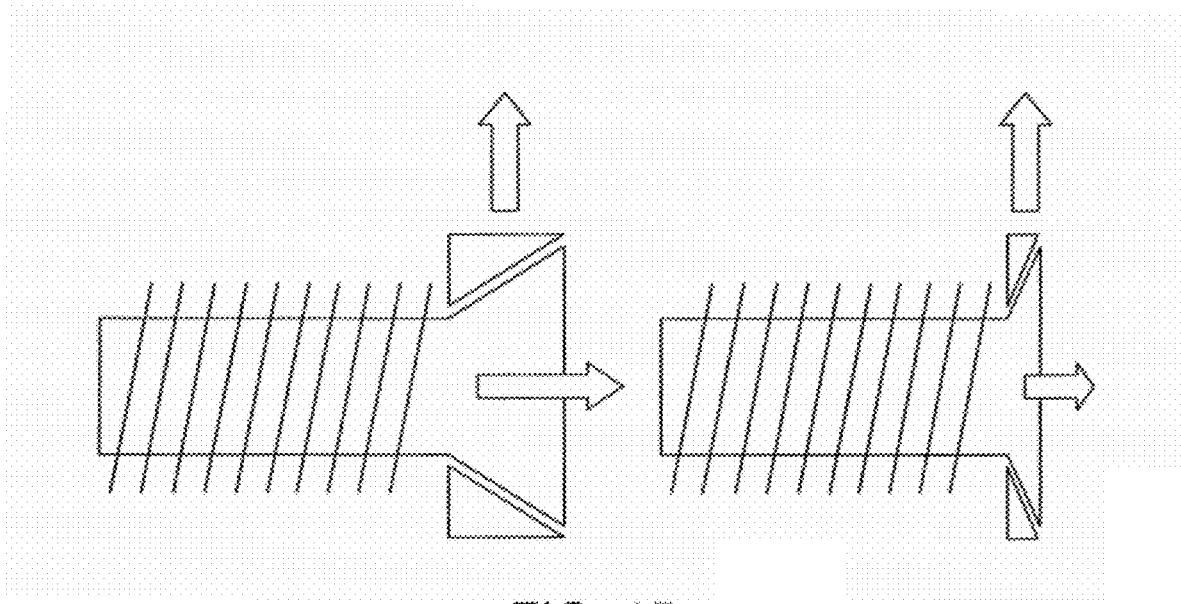
FIG. 15 schematically illustrates the effect of decreased screw head slope and resulting forces.

Results of axial testing have shown that screw head design is an important parameter in system loosening. The screw head design determines the interaction between the screw and the plate. For example, a screw head having a rounded or beveled bottom surface is able to rotate or pivot freely in the plate, as seen in FIG. 14. Instead of moving the plate and screw together, only the screw is loaded. Due to a wedge-type action between the screw and the plate, the screw is forced away from the bone. Axial loading then pull on the screw in a pull-out mechanism instead of lateral loading. The smaller the wedge angle, the less wedge leverage is available to pull the screw out, as seen in FIG. 15.

Figure 16:
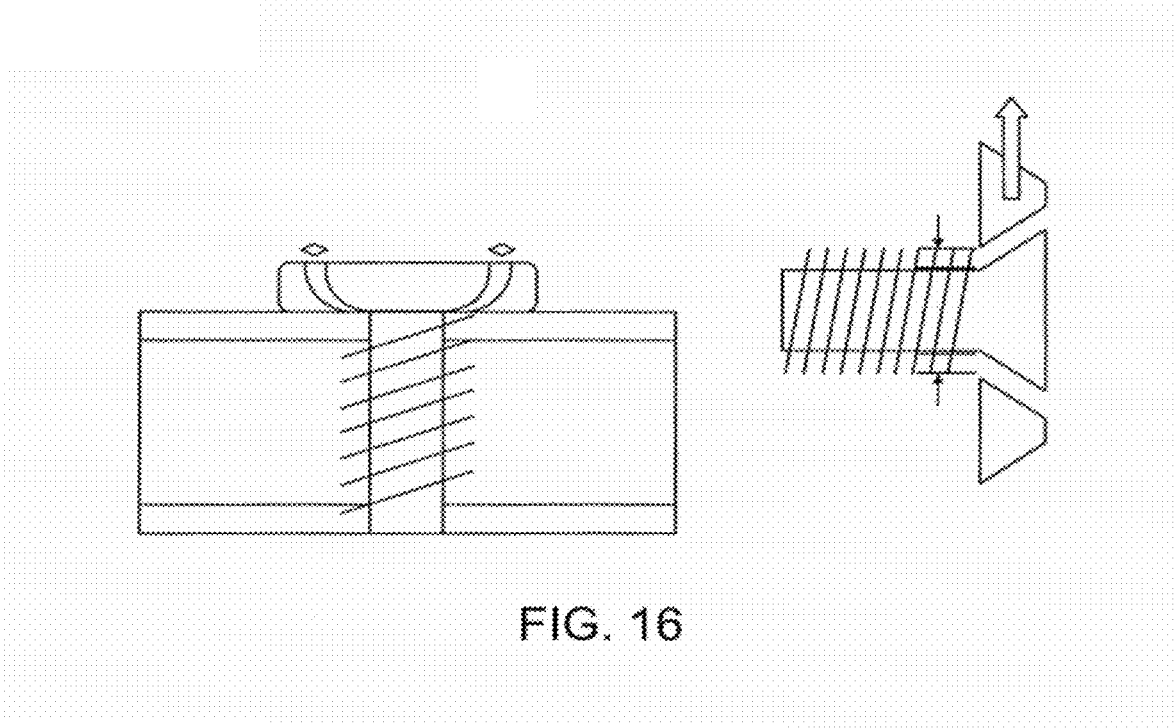
FIG. 16 illustrates screw movement due to plate inner diameter.

Another design parameter observed to have an effect on loosening, particularly loosening due to initial loading, is the difference between the inner diameter of the screw and the inner diameter of the plate. Typically, the minimum inner diameter of the plate hole is the outer diameter of the screw so that the screw can pass through. The screw is centered by the contour of the screw head to the plate. If the threads are deep, the inner diameter of the screw is much smaller than the diameter of the plate hole. During axial loading, the screw will be pulled axially with immediate displacement occurring to the gap between the centered screw and the edge of the plate (FIG. 16).

Figure 17:
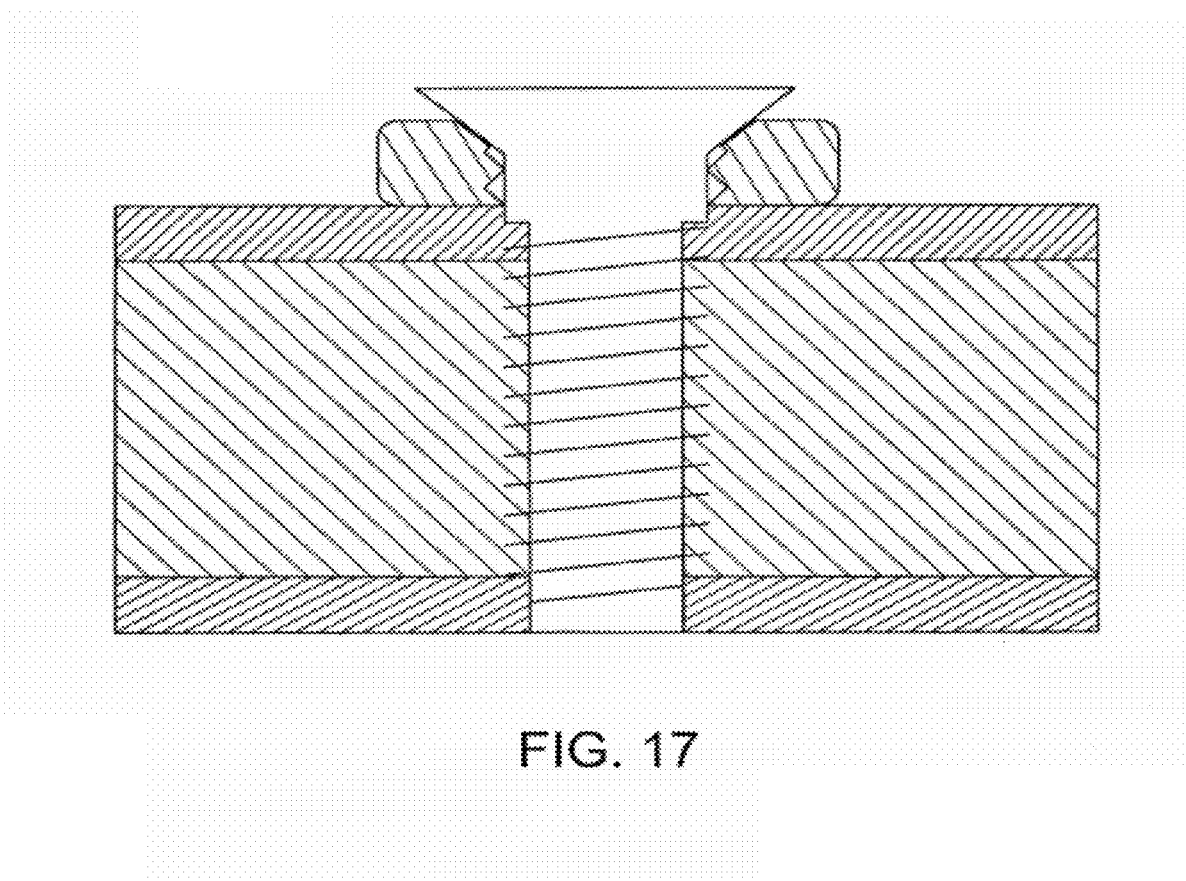
FIG. 17 illustrates a screw and plate assembly with the screw diameter matching the plate hole diameter.

It is therefore concluded that a mechanism that keeps the screw generally perpendicular to the plate is desirable. This mechanism can be provided by a locking screw design; however, the major limitation of locking screws is the inability to control the amount of torque applied to the screw and the purchase into the bone as the torque will be limited by the locking mechanism in the screw head. The locking effect can be achieved by making the inner diameter of the screw as large as the diameter of the plate (FIG. 17). A screw/plate system is proposed in which the plate is threaded to allow the screw threads to pass through. There is a section of the screw right before the screw head that does not have threads but is as wide as the thread diameter, with the concept of having the inner diameter of the screw be as close as possible to the inner diameter of the plate.

The advantages to bicortical purchase include greater ability to tighten the screw to higher torques providing higher plate compressive forces and greater resistance to axial loading. However, in the application of rigid fixation of the sternum, there is a great preference not to use bicortical purchase due to proximity of the heart. There are also problems that arise when trying to use a screw bicortically in osteoporotic bone. Due to the lack of support of cancellous bone in an osteoporotic sternum that only weakly holds the cortical layers together, the second cortical layer can either be drawn upwards (compressing the sternum) or pushed downwards (expanding the sternum) by the screw, thus damaging the bone. If screws are to be used bicortically, then predrilling must also be bicortical, increasing risk of injury to the heart. Therefore, the ability to minimize local distraction with only unicortical purchase is greatly beneficial.

Much of the quantitative data and observed mechanisms of loosening were unexpected. Cortical screws proved to be more resilient against cyclic lateral loading than cancellous even though the sternum is largely structured form trabecular cancellous bone. Though bicortical is generally not an acceptable practice and may cause profound damage to the cancellous region, limiting screw pivoting appears to benefit rigid fixation.

There is still concern of poor press fit from locking screw due to early unwanted locking. However, the non-locking screw results suggest the need for a screw to remain fixed in its complementing plate to limit the screw from pivoting in the plate and loosening. Non-locking screws are able to achieve full press-fit, however, are susceptible to screw pivoting leading to loss of fixation.

There were two concerns of wobbling: non-locking screws pivot within the plate whereas locking screws do not pivot in the plate but can lever the entire plate. The present antiwobble screw-plate assembly combined the needed press-fit to securely fasten the plate against the bone and a locking mechanism to prevent the screw for pivoting in the plate. Testing demonstrated that the combination of full press-fit and locking of the screw to plate significantly reduced the dehiscence produced by lateral cyctic loads more than these each of these mechanisms could do independently.

One embodiment of the present backout-locking system combines the thread density of a cortical screw with cancellous thread blades to maximize contact with the cortical bone layer. The screw head incorporates the antiwobble concept and is designed to toggle between a non-locking and locking mode within the plate compartment. This allows for the user to fasten the screw without any plate restriction to achieve full press-fit and to follow-up with locking the head into the plate to prevent pivoting. The overall findings and observations indicate the best option of rigid plate fixation for osteoporotic sternum is the backout-locking screw-plate system.

A further preferred embodiment of the invention utilizes a two piece screw assembly, sternal fixation plates and requires only one tool for surgical installation. The screw is also unicortical and of both the compression and locking type. The two part design is a screw within a screw and was designed to optimize two important functional considerations: ease of use by the surgeon and manufacturability.

Figure 18B:
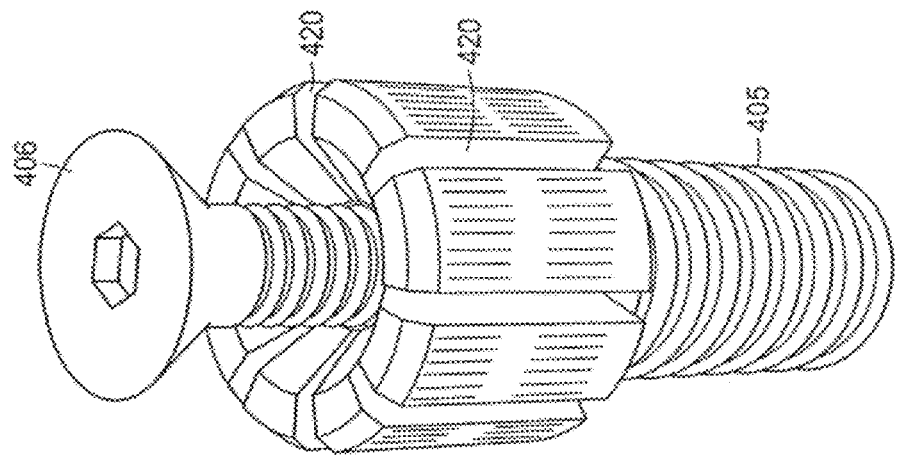
FIG. 18B illustrates a perspective view of a locking screw assembly in accordance with the invention.
Figure 18A:
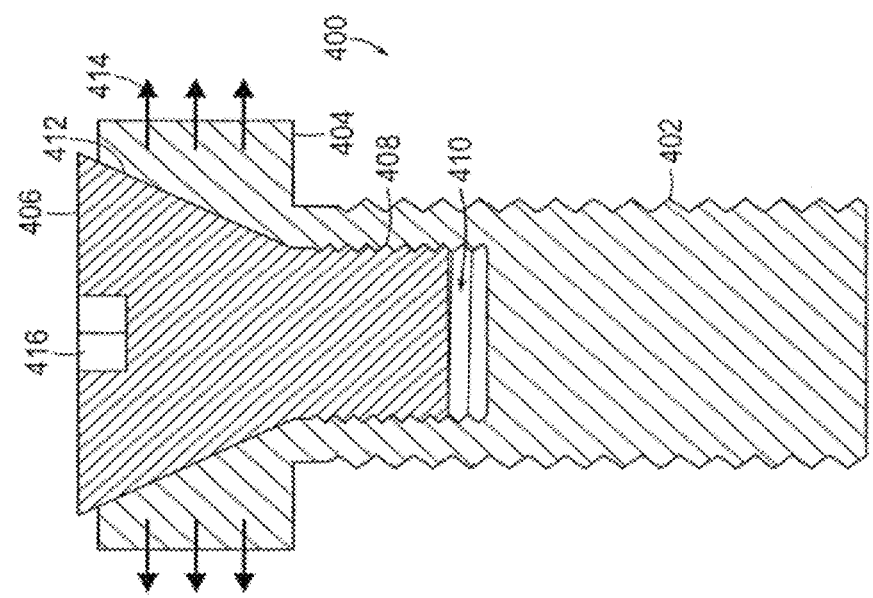
FIG. 18A illustrates a preferred embodiment of a locking screw assembly in accordance with the invention.

The outer screw functions as a compression unicortical screw with a screw head-plate interface. As seen in FIG. 18A, the outer screw has a countersunk head with radial expansion slits around its circumference. The bottom of the countersunk hole has receiving threads for the internal screw. A unicortical thread pattern on the distal bone interfacing screw body is employed as well as a self-tapping tip. The bottom of the outer screw head can have a roughened surface that will interface with the bottom of the plate welling.

The inner screw mates into the top of the outer screw with its wedge pitch being the same angle as the outer screw's receiving countersink, but the wedge length will extend past the top of the outer screw. A standard Phillips head surgical tool can be used to interface with top of the internal screw.

When the threaded shaft of the inner screw is mated with the female threads on the inside of the outer screw, and gently tightened, it is pulled down into the body of the outer screw. This is the state of the device at which the surgeon will receive it. The screw is then inserted into the plate and bone through normal surgical procedure. When the screw has reached a tightness determined by the surgeon for compression fit of the plate to the bone, the surgeon exerts a downward force to engage the roughened outer screw head's bottom surface with the fixation plate's well surface. This creates enough of a frictional force to allow the inner screw to continue to rotate into the outer screw internal body (and without stripping the bone), thus creating an outward wedging force on the outer screw head. The expansion slits allow the head of the outer screw to expand into the walls of the plate, causing a force induced locking mechanism that holds the screw tightly at the plate interface.

As seen in FIG. 18A, a stainless steel flat head screw was used as the inner screw 406, which pushes against a modified stainless steel socket head cap screw 402. As seen in FIG. 18B, expansion slots 420 in an expansion portion 404 of the screw allow the user to insert the threaded portion 405 through a plate and into bone as described previously herein. The inner screw 406 in then tightened by the surgeon using notch 416 to drive the threaded portion 408 further into the inner cavity 410 of the screw 402. Surface 412 of screw 406 imparts a lateral force to move 414 the expansion portion in a lateral direction to frictionally engage the plate.

A screw-plate system manufactured where the outer screw can successfully be press-fit and locked into the stainless steel plate. As the inner screw is tightened, the outer screw splays out and frictionally engages the stainless steel plate, which prevents micro motion of the screw head with the plate. This reduces the wobbling effect and minimize screw loosening against the bone.

A preferred method of manufacture involves using 2.3 mm non-locking unicortical bone screw to act as the outer screw with a smaller 1.75 mm standard screw. In order to manufacture such a small system, wire electrical discharge machining is performed to create small cuts in the head of the outer screw. Furthermore, the outer screw will be tapped with a thread mill to create a threaded hole for the inner screw to be inserted. The standard bone plate will not be modified, as the outer screw will expand and press-fit against the plate.

The effectiveness of the designed screw plate system has been determined by comparing it to unicortical non-locking screw plate systems. Both systems were cyclically loaded to mimic breathing of a normal human being to assess the amount of screw displacement.

While the invention has been described in connection with specific methods and apparatus, those skilled in the art will recognize other equivalents to the specific embodiments herein. It is to be understood that the description is by way of example and not as a limitation to the scope of the invention and these equivalents are intended to be encompassed by the claims set forth below.

What is claimed is:

1. A method of sternal bone fixation comprising:
inserting a plurality of screws into bone to attach a plate to a sternum of a patient, each of the screws having a threaded portion and a screw head, each screw head including a radially expandable portion and a bottom friction surface to engage a plate surface positioned underneath the radially expandable portion of the screw head; and
locking each of the screws to the plate with the bottom friction surface associated with each screw head such that the radially expandable portion of each screw is displaced radially above the plate surface and relative to the threaded portion of each screw.

2. The method of claim 1 further comprising attaching a first sternum bone to a second sternum bone.

3. The method of claim 2 further comprising using a plurality of plates to attach the first sternum bone to the second sternum bone.

4. The method of claim 1 further comprising inserting each screw into a cortical layer and a cancellous bone layer.

5. The method of claim 4 further comprising inserting each screw into a second cortical layer.

6. The method of claim 1 wherein each screw attaches to bone with a thread spacing in a range of 1 mm to 1.25 mm.

7. The method of claim 1 further comprising rotating each screw into a bone until a screw flange engages the plate and the plate contacts the bone.

8. The method of claim 1 further comprising actuating the radially expandable portion of each screw to frictionally engage the plate and each screw.

9. The method of claim 8 further comprising actuating the radially expandable portion by turning a threaded shaft into an internally threaded section of the screw, the screw having vertical slots.

10. The method of claim 1 further comprising inserting the plurality of screws through the plate and into the bone, each screw having a length in a range of 0.4 to 1.4 cm.

11. The method of claim 1 further comprising displacing a first portion of each screw head relative to a second portion of a screw head to lock the screw to the plate.

12. The method of claim 1 further comprising inserting each screw to expand a portion of a screw head to lock the screw to the plate.

13. The method of claim 1 wherein the plate comprises a two dimensional distribution of holes to receive the plurality of screws.

14. The method of claim 1 wherein the plate has at least two holes to attach to one side of a patient's sternum and at least a further two holes to attach to the plate to a second side of the sternum.

* * * * *